United States Patent

Takahashi et al.

[11] Patent Number: 5,639,903
[45] Date of Patent: Jun. 17, 1997

[54] SULFONIUM SALT COMPOUNDS AND INITIATORS OF POLYMERIZATION

[75] Inventors: Eiji Takahashi; Hiroo Muramoto, both of Chiba, Japan

[73] Assignee: Nippon Soda Co., Ltd., Tokyo, Japan

[21] Appl. No.: 569,217

[22] PCT Filed: Jun. 14, 1994

[86] PCT No.: PCT/JP94/00953

§ 371 Date: Dec. 11, 1995

§ 102(e) Date: Dec. 11, 1995

[87] PCT Pub. No.: WO94/29271

PCT Pub. Date: Dec. 22, 1994

[30] Foreign Application Priority Data

Jun. 15, 1993 [JP] Japan ................ 5-168568

[51] Int. Cl.$^6$ .................................. C07C 321/00
[52] U.S. Cl. ...................... 560/15; 560/10; 560/17; 560/18; 560/47; 560/254; 562/431; 568/55; 568/39; 568/58; 568/46
[58] Field of Search ................ 560/15, 254, 18, 560/17, 10, 47, 85; 568/55, 39, 58, 46; 562/431

[56] References Cited

FOREIGN PATENT DOCUMENTS 3-176428  7/1991  Japan .

*Primary Examiner*—Samuel Barts
*Attorney, Agent, or Firm*—Joseph C. Mason, Jr.; Louise A. Foutch

[57] ABSTRACT

The present invention is related to sulfonium salt compounds useful as an initiator of cationic polymerization and represented by a following general formula (I):

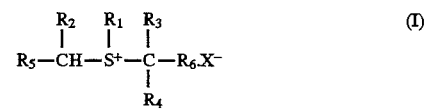

wherein $R_1$ is benzyl, phenyl, etc., $R_2$, $R_3$ and $R_4$ are each independently hydrogen, alkyl, etc., $R_5$ is hydrogen, alkyl, phenyl, etc., $R_6$ is a group represented by a formula, $-(CH_2)_m-R_{11}$ wherein $R_{11}$ is $COR_{12}$, $COOR_{13}$, $OR_{14}$, nitrile, $OCOR_{15}$ or $SOR_{16}$, wherein $R_{12}$, $R_{13}$, $R_{14}$, $R_{15}$ and $R_{16}$ are each independently hydrogen, alkyl or phenyl, m is 0 or 1, and X represents $SbF_6$, $AsF_6$, $PF_6$ or $BF_4$.

2 Claims, No Drawings

SULFONIUM SALT COMPOUNDS AND INITIATORS OF POLYMERIZATION

This application is a 371 of PCT/JP94/00953 filed Jun. 14, 1994.

FIELD OF THE INVENTION

The present invention is related to novel sulfonium salt compounds and initiators of cationic polymerization comprising said sulfonium salt compound. The cationic polymerizable composition comprising said initiator of polymerization can cure under heating in a short time, and the cured-product thereof shows to have excellent physical properties. Therefore, the cationic polymerizable composition can be suitably used for molding resins, casting resins, coating materials, adhesives, inks and so on.

BACKGROUND ART

As curing agents for epoxy resins, amine-containing compounds, carboxylic anhydride and mercapto compounds, all of which are being widely used for two-part system, have been known. In two-part system, however, it is necessary to mix each components in absolutely uniform, and time for several hours are required for resulting the curing.

In addition, there is another problem in the curing in two-part system such as difficulty in the production because of its short pot life as long as from several hours to several days due to consecutive continuance of curing reaction proceeding even at room temperature.

Whereas, boron fluoride and monoethyl amine combination have been known as an agent for curing epoxy resins in one-part system. However, there are problems in the curing such that temperature required for the curing is very high as much as 160° C. and time duration of from 1 to 8 hours is required for the completion of the curing.

Aiming at solving such problems described above, pyridinium salt compounds are disclosed in JP Laid-Opened No. Hei 1-299270. By using pyridinium salt compounds, the execution of curing in one-part system and shortening of time required for the curing could have been realized, however, another problem of high temperature required for the curing has not been improved.

Further to said pyridinium salt compounds, the following sulfonium salt compounds similar to the compounds specified in the present invention have been disclosed.

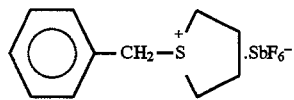

(JP Laid-Opened No. Hei 2-178319)

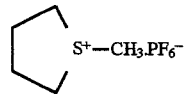

(JP Patent Examined Gazette No. Sho 63-12092)

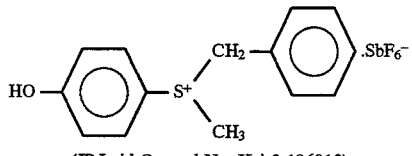

(JP Laid-Opened No. Hei 2-196812)

However, sulfonium salt compounds disclosed in both JP Laid-Opened No. 2-178319 and JP Patent Examined Gazette No. Sho 63-12092 are still requiring high temperature to complete curing, and therefore, it is difficult to obtain cured-products having good physical property when using epoxy resins being widely used, such as bisphenol A diglycidyl ether.

Besides, sulfonium salt compounds described in JP Patent Examined Gazette No. Sho 63-12092 are mostly prepared from sulfide compounds having low boiling point, and therefore, the sulfonium salt compound itself and the cured-product thereof give bad smell in most cases.

On the other hand, sulfonium salt compounds described in JP Laid-Opened No. Hei 2-196812 are prepared from aromatic sulfide compounds in solid, and therefore, those sulfonium salt compounds do not give bad smell. However, because of their physical state in solid, said sulfonium salt compounds have a problem in the solubility in monomer. In addition, physical properties of the cured-products therewith tend to be no good. Furthermore, it is not easy to use sulfonium salt compounds capable of curing resins at less than 150° C. in one-part system.

DISCLOSURE OF THE INVENTION

The inventors of the present invention had examined to find novel initiators of polymerization which do not have problems such as giving smell, can cure cationic polymerizable compounds in a short time at a low temperature, and can further furnish excellent physical properties to the cured-product therewith, thereby having completed the present invention.

Therefore, the present invention is directed to sulfonium salt compounds represented by a general formula (I);

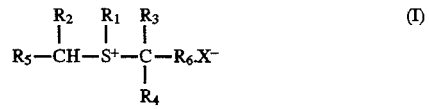

wherein $R_1$ is unsubstituted or substituted benzyl, unsubstituted or substituted naphthylmethyl, unsubstituted or substituted cinnamyl, 9-fluorenyl, or unsubstituted or substituted phenyl, $R_2$ and $R_3$ are each independently hydrogen or alkyl;

$R_4$ is hydrogen, alkyl or phenyl, $R_5$ is hydrogen, alkyl, alkenyl, phenyl or —$(CH_2)_n$—$R_7$ wherein $R_7$ is $COOR_8$, $OR_9$, nitrile or $OCOR_{10}$, wherein $R_8$, $R_9$ and $R_{10}$ are each independently hydrogen, unsubstituted or substituted alkyl, or phenyl, and n denotes 0 or 1, $R_6$ is —$(CH_2)_m$—$R_{11}$ wherein $R_{11}$ is $COR_{12}$, $COOR_{13}$, $OR_{14}$, nitrile, $OCOR_{15}$ or $SOR_{16}$, wherein $R_{13}$, $R_{14}$, $R_{15}$ and $R_{16}$ are each independently unsubstituted or substituted alkyl or phenyl, and m denotes 0 or 1, and X is $Sb_6$, $AsF_6$, $PF_6$ or $BF_4$, and initiators of cationic polymerization.

As substituents for each aromatic ring of benzyl, naphthylmethyl, cinnamyl and phenyl as represented by $R_1$, alkyl, such as methyl, ethyl, propyl and butyl, halogen, such as fluorine, chlorine, bromine and iodine, nitro, vinyl, hydroxy, alkoxy, such as methoxy and ethoxy, alkanoyl, such as methoxycarbonyl and phenoxycarbonyl, and acyl, such as acetoxy and benzoyl, can be exemplified.

Further, as substituents for α-position of benzyl, alkyl, such as methyl, ethyl, propyl and butyl, halogen, such as fluorine, chlorine, bromine and iodine, alkanoyl, such as methoxycarbonyl and phenoxycarbonyl, and phenyl, can be exemplified.

As substituents for alkyl as represented by $R_8$, $R_9$, $R_{10}$, $R_{12}$, $R_{13}$, $R_{14}$, $R_{15}$ and $R_{16}$, halogen, such as fluorine, chlorine, bromine and iodine, nitro, alkoxy, such as methoxy and ethoxy, vinyl, phenyl and the like can be exemplified. In addition, among the substituents recited above, alkyl, alkoxy, phenyl, etc. may be substituted by the same substituents as described above. Again, as substituents for phenyl, alkyl, such as methyl, ethyl, propyl and butyl, halogen, such as fluorine, chlorine, bromine and iodine, nitro, alkoxy, such as methoxy and ethoxy, and cyano can be exemplified.

For X, $SbF_6$ is the most preferable group among $SbF_6$, $AsF_6$, $PF_6$ and $BF_4$.

The sulfonium salt compounds of the present invention can be obtained according to reaction equations as shown hereinbelow.

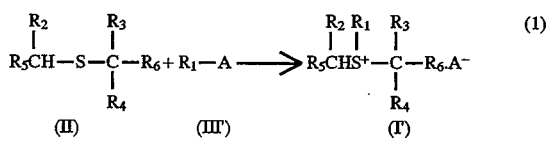
(1)

wherein A is halogen or

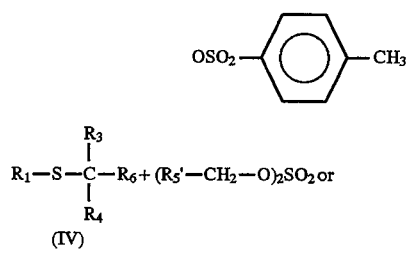
(IV)

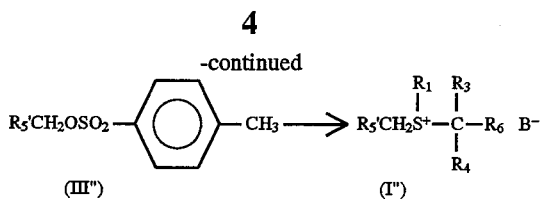

wherein $R_5'$ is hydrogen or lower alkyl,

B is $R_5'$—$CH_2OSO_3$ or

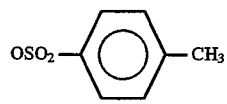

Both reactions of (1) and (2) are carried out for the time duration of from several hours to a dozen of days at a temperature of from room temperature to 80° C., and in an organic solvent, such as methanol, acetonitrile and dioxane, if required. Also, it is preferable to carry out the reactions by using each compounds being in approximately equimolar concentration, respectively.

The objective compounds can be obtained by passing sequential procedure comprising of dissolving the compounds having formulas (I') and (II") obtained by the reactions as described above into water or water-organic solvent system, such as water-methanol, adding a compound represented by a general formula MX(V), wherein M denotes an alkaline metal, to the solution to allow to stand in a reaction while stirring vigorously, and separating precipitated-substance in liquid or solid state.

For the representative examples of the sulfonium salt compounds of the present invention, the followings are exemplified. In each formulas, X represents any of $SbF_6$, $AsF_6$, $PF_6$ or $BF_4$.

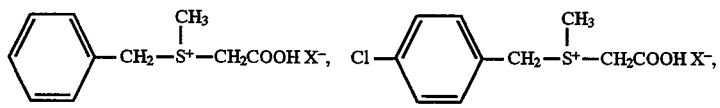

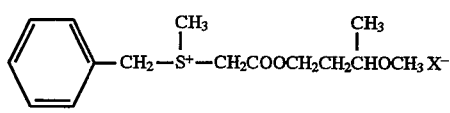

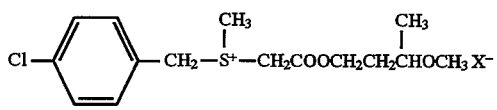

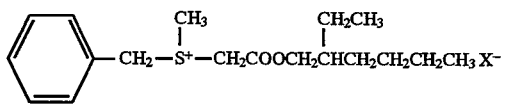

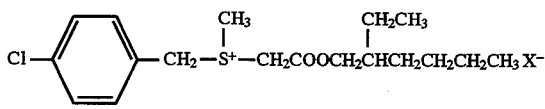

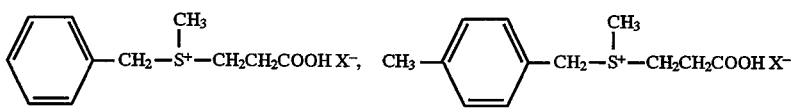

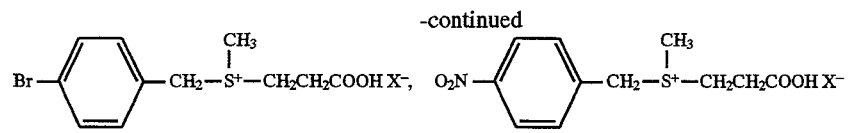
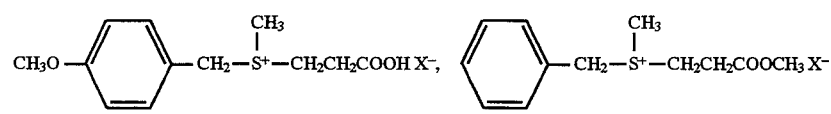
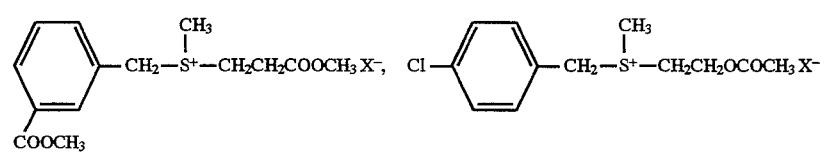
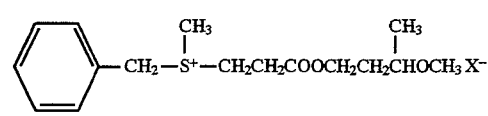
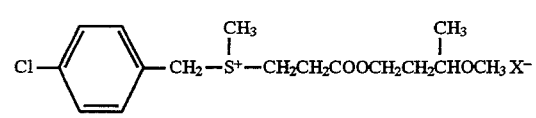
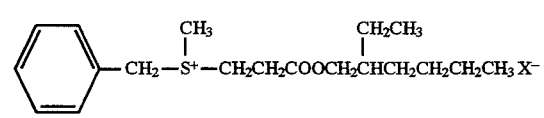
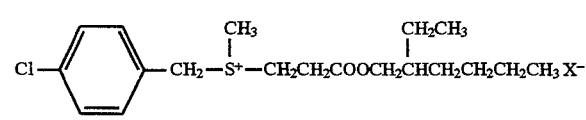
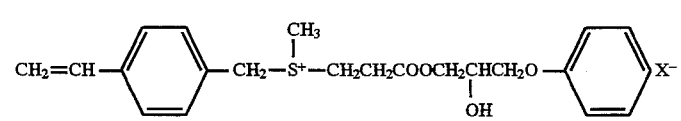
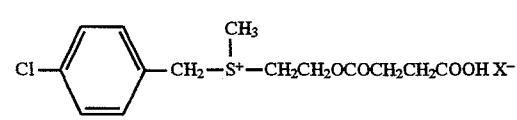
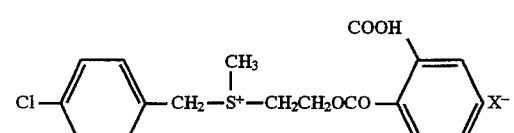
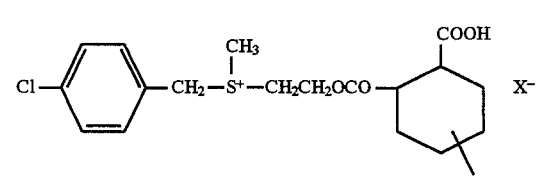
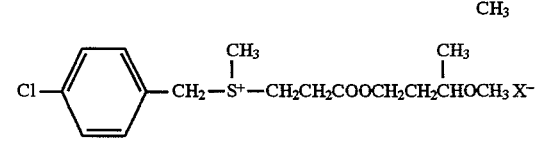
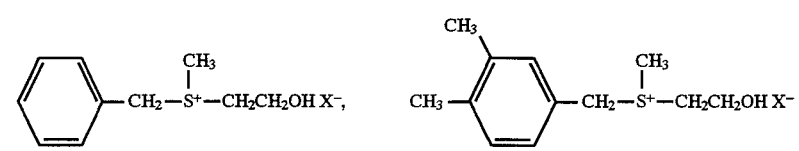

-continued
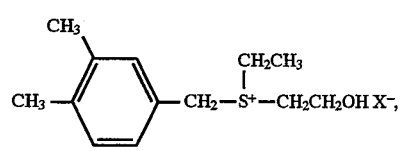 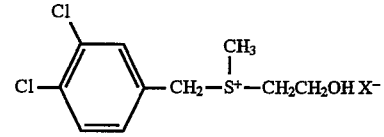
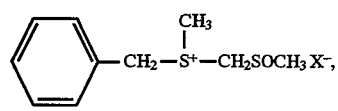 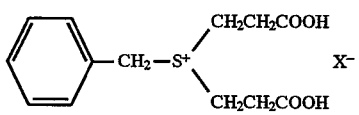
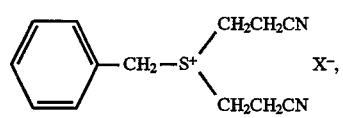 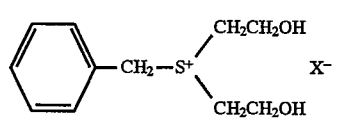
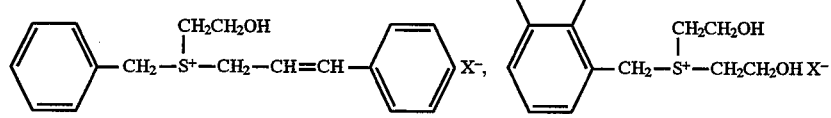
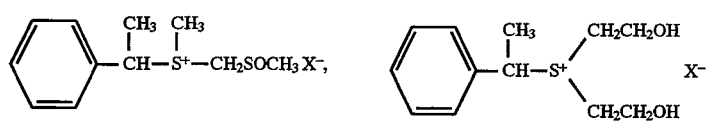
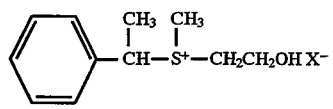
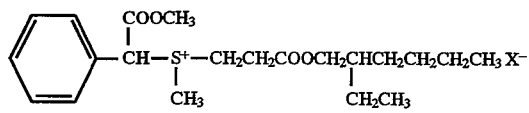
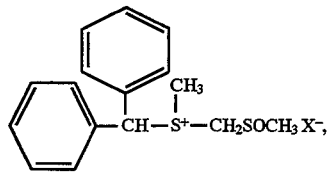 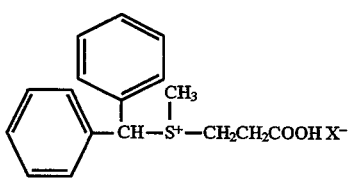
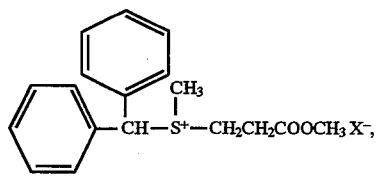 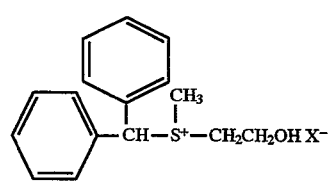
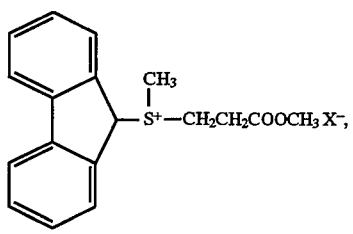 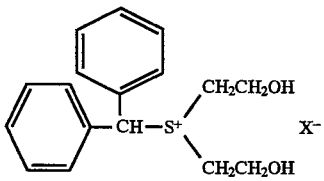
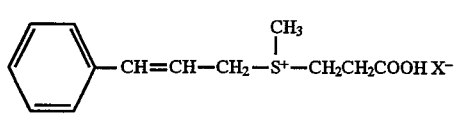

-continued

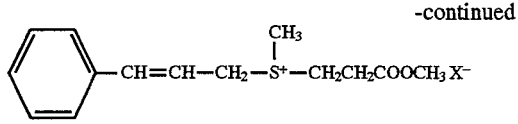

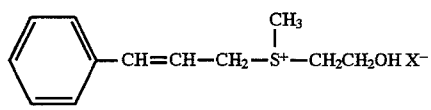

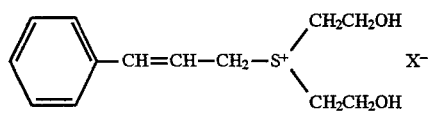

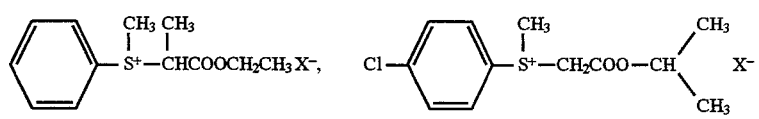

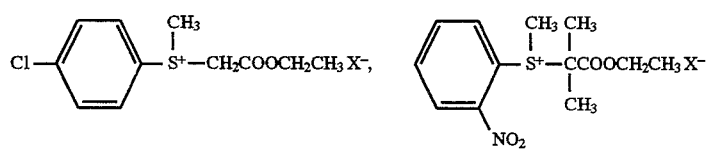

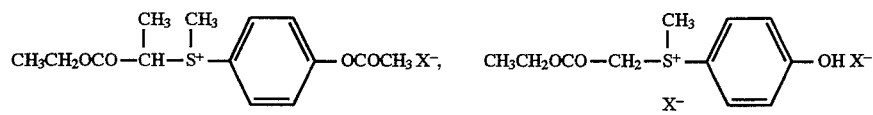

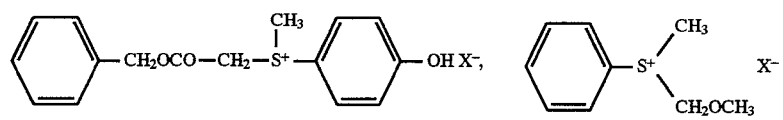

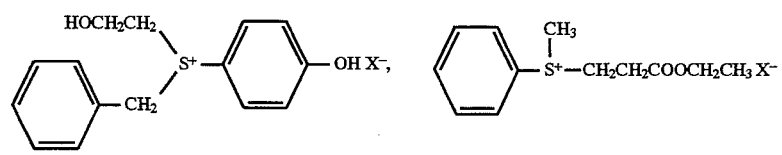

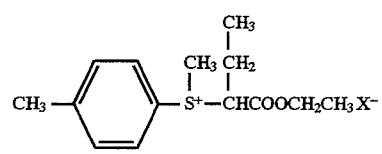

In the present invention, a compounding ratio of the sulfonium salt compound respective to 100 parts of the cationic polymerizable compound is in a range of from 0.01 to 20 parts, and preferably from 0.1 to 10 parts. If said compounding ratio is less than the above range, curing capability of the cationic polymerizable compound deteriorates, while the advantageous physical property of the cured-product deteriorates if said compounding rate exceeds the above range.

The cationic polymerizable compound comprising the sulfonium salt compound of the present invention can be easily cured under heating.

For carrying out thermo-setting, a temperature in a range of from 30° to 200° C., preferably from 50° to 180° C., can be applied.

The cationic polymerizable compound comprising the sulfonium salt compound of the present invention can be easily cured in a short time under irradiation with ionizing radiation, such as α-ray, β-ray, γ-ray, neutron beam, X-ray and accelerating electronic ray. For curing the cationic polymerizable compound with ionizing radiation, a radiation dose of from 0.5 to 60M rad, and preferably from 1 to 50M rad, is normally applied to the compound.

In addition, it is also possible to result photo-setting of the cationic polymerizable compounds comprising the sulfonium salt compound of the present invention by additionally using a phenol sensitizer, such as 4-methoxy phenol, 4-methoxy-l-naphthol and 2-hydroxy benzofuran, or an aromatic secondary or tertiary amine sensitizer, such as phenothiazine, N,N'-diphenyl-p-phenylenediamine and N,N'-dimethylamino ethyl benzoate, in combination with the sulfonium salt compound.

The sulfonium salt compound of the present invention is normally used alone, but it may also be used in combination with other initiator of cationic polymerization. Also, the sulfonium salt compounds of the present invention may be used with any adding of reactive diluent, cure accelerator, solvent, pigment, dye, coupling agent, inorganic filler, carbon fiber, glass fiber and surface active agent.

The initiator of polymerization of the present invention is a type suitable for chain polymerization, and therefore, it can result polymerization and curing of cationic polymerizable compounds in a short time. Furthermore, the initiator itself gives less smell or almost no-smell since it contains groups, such as hydroxy, carboxy, ester and sulfinyl, in the molecule, and decomposed-product of the initiator gives less smell or no-smell as well. Moreover, the initiator of polymerization containing those groups as described above tends to have good solubility in monomer, and cationic polymerizable compound comprising said initiator acquires improved storage stability. In addition thereto, by changing the substituents in the chemical formula of the initiator, it becomes possible to set an optional curing temperature, thereby allowing the cured-product to have excellent physical property owing to the decrease of inhibitory effect on cationic polymerization caused by the decomposed-product of the initiator being remained.

BEST MODE FOR CARRYING OUT THE INVENTION

Now, the present invention is further described with referring to Examples and Comparative Examples. However, it should be noted that the present invention shall not be limited to the scope specified in the Examples described hereinbelow.

EXAMPLE 1

Synthesis of methyl-sulfonylmethylbenzylmethyl sulfonium hexafluoroantimonate (Compound No. 1)

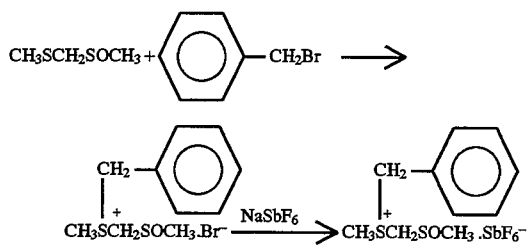

6.21 g of methylmethylsulfinylmethyl sulfide and 17.10 g of benzyl bromide were mixed, and were then allowed to stand in reaction at 50° C. for five months. The compound obtained was washed with ether, dried at 40° C. under reduced pressure, affording a precursor, methylsulfinylmethylbenzylmethyl sulfonium bromide. Yield: 26%.

1.48 g of methylsulfinylmethylbenzylmethyl sulfonium bromide was dissolved into a mixed solution of 5 g of distilled water and 2 g of ethyl ketone (herein after referred to as MEK). Then, 1.55 g of sodium hexafluoroantimonate was added to the solution, then stirred throughly. To this solution, 45 g of distilled water was added, then the solution was stirred throughly and subsequently cooled. The compound precipitated was separated by filtration, then dried at 40° C. under reduced pressure. Yield: 56%

Spectral data of the compound obtained was as follows.

IR(KBr, cm$^{-1}$): 3038, 1498, 1458, 1428, 1050, 775, 706, 660

EXAMPLE 2

2-hydroxyethylbenzylmethyl sulfonium hexafluoroantimonate (Compound No. 3)

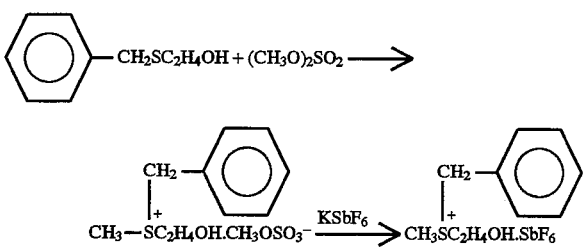

8.41 g of 4-hydroxyethylbenzyl sulfide and 6.31 g of dimethyl sulfuric acid were mixed, then allowed to stand in reaction at 50° C. for seven days. The compound obtained was washed with ether, dried at 40° C. under reduced pressure, affording a precursor, 2-hydroxyethylbenzylmethyl sulfonium sulfate. Yield: 99%.

2.94 g of 2-hydroxyethylbenzylmethyl sulfonium sulfate was dissolved into a 15 g of distilled water. To this solution, 3.30 g of sodium hexafluoroantimo nate was added, then the solution was stirred throughly and subsequently cooled.

The compound precipitated in the solution was separated and was then dried at 40° C. under reduced pressure. Yield: 71%

Spectral data of the compound obtained was as follows.

IR(KBr, cm$^{-1}$): 3580, 1498, 1458, 1424, 1068, 773, 704, 660

The representative examples of the compounds of the present invention prepared according to the same procedure as described above are shown in Table 1, including the compounds prepared in the Examples 1 and 2.

TABLE 1

Structural formula $$R_5-CH(R_2)-S^+(R_1)-C(R_3)(R_4)-R_6 \quad X^-$$

| Compound No. | $R_1$ | $R_2$ | $R_3$ | $R_4$ | $R_5$ | $R_6$ | X | Physical Constant IR (KBr cm$^{-1}$) |
|---|---|---|---|---|---|---|---|---|
| 1 | ⌬—CH$_2$— | H | H | H | H | SOCH$_3$ | SbF$_6$ | 3038, 1498, 1458 1428, 1050, 775 706, 660 |

TABLE 1-continued

Structural formula $$R_5-CH-S^+-C-R_6 \quad X^-$$

with $R_2$ on CH, $R_1$ on S, $R_3$ and $R_4$ on C

| Compound No. | $R_1$ | $R_2$ | $R_3$ | $R_4$ | $R_5$ | $R_6$ | X | Physical Constant IR (KBr cm$^{-1}$) |
|---|---|---|---|---|---|---|---|---|
| 2 | phenyl-CH$_2$- | H | H | H | H | CH$_2$CO$_2$H | SbF$_6$ | 1723, 1498, 1458 1423, 1251, 1189 773, 704, 660 |
| 3 | phenyl-CH$_2$- | H | H | H | H | CH$_2$OH | SbF$_6$ | 3580, 1498, 1458 1424, 1068, 773 704, 660 |
| 4 | HO-phenyl- | H | H | H | phenyl- | CH$_2$OH | SbF$_6$ | 3495, 1600, 1585 1500, 1457, 1436 1288, 1213, 1179 1087, 888, 770 703, 662 |
| 5 | phenyl-CH$_2$- | H | H | H | HOCH$_2$ | CH$_2$OH | SbF$_6$ | 3570, 1497, 1456 1420, 1365 1116 752, 703, 660 |
| 6 | Br-phenyl-CH$_2$- | H | H | H | H | CH$_2$CO$_2$H | SbF$_6$ | 1718, 1594, 1490 1435, 1271, 1221 1070, 1013, 841 725, 660 |
| 7 | 3,5-(CH$_3$)$_2$-phenyl-CH$_2$- | H | H | H | H | CH$_2$OH | SbF$_6$ | 3577, 2944, 1505 1457, 1424, 1119 1069, 830, 660 |
| 8 | 3,4-Cl$_2$-phenyl-CH$_2$- | H | H | H | H | CH$_2$OH | SbF$_6$ | 3581, 1474, 1425 1400, 1209, 1138 1035, 831, 660 |
| 9 | 2,5-(CH$_3$)$_2$-phenyl-CH$_2$- | H | H | H | CH$_3$ | CH$_2$OH | SbF$_6$ | 3573, 2979, 2944 1505, 1456, 1423 1119, 829, 661 |
| 10 | phenyl-CH$_2$- | H | H | H | H | CH$_2$CO$_2$CH$_3$ | SbF$_6$ | 3032, 1735, 1496 1440, 1373, 1244 1210, 710, 660 |
| 11 | Cl-phenyl-CH$_2$- | H | H | H | H | CH$_2$OCOCH$_3$ | SbF$_6$ | 3029, 1747, 1598 1495, 1426, 1388 1230, 1097, 843 660 |
| 12 | phenyl-CH=CHCH$_2$- | H | H | H | phenyl- | CH$_2$OH | SbF$_6$ | 3572, 2966, 1659 1609, 1496, 1457 1415, 1285, 1108 1067, 907, 770 775, 709, 658 |
| 13 | phenyl-CH$_2$- | H | H | H | H | C$_2$H$_5$ \| CO$_2$CH$_2$CHC$_4$H$_9$ | SbF$_6$ | 2933, 1738, 1498 1459, 1425, 1384 1318, 1244, 1203 1002, 768, 703 662 |

TABLE 1-continued

Structural formula $$R_5-CH-S^+-C-R_6 \quad X^-$$
with $R_2$ on CH, $R_1$ and $R_3$ on C, $R_4$ on C

| Compound No. | R₁ | R₂ | R₃ | R₄ | R₅ | R₆ | X | Physical Constant IR (KBr cm⁻¹) |
|---|---|---|---|---|---|---|---|---|
| 14 | Ph-CH(CH₃)- | H | H | H | H | CH₂OH | SbF₆ | 3544, 3035, 1481 1425, 1120, 1049 753, 661 |
| 15 | (Ph)₂CH- | H | H | H | H | CH₂CO₂H | SbF₆ | 3035, 1723, 1495 1424, 1349, 1244 1198, 1165, 1046 754, 660 |
| 16 | (Ph)₂CH- | H | H | H | H | CH₂CO₂CH₃ | SbF₆ | 3033, 1738, 1493 1440, 1374, 1245 1211, 1047, 752 702, 660 |
| 17 | (2,2'-biphenyl)CH- | H | H | H | H | CH₂CO₂CH₃ | SbF₆ | 3035, 1738, 1440 1374, 1246, 1211 1046, 740, 659 |
| 18 | (Ph)₂CH- | H | H | H | H | CH₂OH | SbF₆ | 3559, 3033, 1600 1425, 1119, 1049 754, 701, 659 |
| 19 | Ph-CH=CHCH₂- | H | H | H | H | CH₂CO₂H | SbF₆ | 3030, 1718, 1647 1600, 1494, 1418 1245, 1193, 977 757, 701, 661 |
| 20 | Ph-CH=CHCH₂- | H | H | H | H | CH₂OH | SbF₆ | 3573, 1599, 1494 1423, 1118, 1063 976, 757, 705 660 |
| 21 | (naphthyl)-CH₂- | H | H | H | H | CH₂OH | SbF₆ | 3575, 1598, 1513 1423, 1117, 1071 806, 781, 661 |
| 22 | Ph- | H | H | H | H | CH₂CO₂C₂H₅ | SbF₆ | 1727, 1480, 1450 1425, 1379, 1267 1197, 983, 760 657 |

TABLE 1-continued

Structural formula $$R_5-\underset{\underset{H}{|}}{C}H-\underset{}{S^+}-\underset{\underset{R_4}{|}}{\overset{\overset{R_3}{|}}{C}}-R_6 \quad X^-$$

with $R_2$ on CH and $R_1$ on $S^+$

| Compound No. | $R_1$ | $R_2$ | $R_3$ | $R_4$ | $R_5$ | $R_6$ | X | Physical Constant IR (KBr cm$^{-1}$) |
|---|---|---|---|---|---|---|---|---|
| 23 |  | H | H | H | H | $CH_2CO_2C_2H_5$ | $SbF_6$ | 2945, 1736, 1577 1482, 1399, 1318 1279, 1202, 1098 1013, 828, 749 661 |
| 24 | 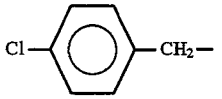 | H | H | H | H | $\underset{|}{\overset{C_2H_5}{CH_2CO_2CHC_4H_9}}$ | $SbF_6$ | 2960, 1732, 1598 1494, 1464, 1413 1372, 1241, 1207 1097, 1017, 843 732, 661 |
| 25 | 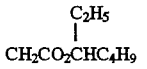 | H | H | H | H | $CH_2OCOC_2H_4CO_2H$ | $SbF_6$ | 2953, 1734, 1598 1497, 1413, 1360 1208, 1159, 1097 1018, 845, 733 661 |
| 26 | 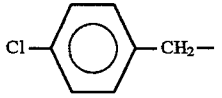 | H | H | H | H | 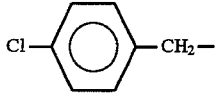 | $SbF_6$ | 2951, 1724, 1599 1494, 1413, 1286 1261, 1201, 1125 1077, 1017, 746 661 |
| 27 | 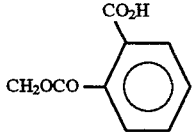 | H | H | H | H | $\underset{|}{\overset{OCH_3}{CH_2CO_2C_2H_4CHCH_3}}$ | $SbF_6$ | 2973, 1733, 1498 1458, 1424, 1373 1243, 1205, 1081 773, 705, 660 |
| 28 | 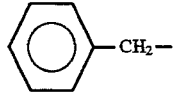 | H | H | H | H | $\underset{|}{\overset{C_2H_5}{CH_2CO_2CH_2CHC_4H_9}}$ | $SbF_6$ | 2960, 1732, 1459 1399, 1372, 1309 1240, 1201, 1016 728, 661 |
| 29 | 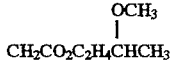 | H | H | H | H | $CO_2C_2H_5$ | $SbF_6$ | 3488, 1736, 1602 1587, 1503, 1438 1317, 1290, 1202 1181, 1019, 838 661 |
| 30 | 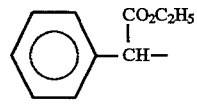 | H | H | H | H | 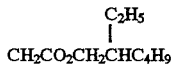 | $SbF_6$ | 3516, 1729, 1602 1588, 1502, 1441 1286, 1219, 1181 1091, 997, 841 663 |
| 31 | 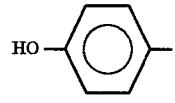 | H | H | H | H | $OCH_3$ | $SbF_6$ | 3035, 2941, 1593 1494, 1427, 1045 999, 751, 658 |
| 32 | 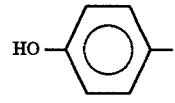 | H | H | H | H | $CH_2CO_2C_2H_5$ | $SbF_6$ | 1733, 1601, 1585 1503, 1450, 1372 1294, 1198, 1084 1014, 841, 661 |
| 33 | 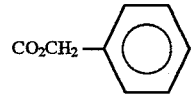 | H | H | H | $HO_2C-CH_2-$ | $CH_2CO_2H$ | $SbF_6$ | 3032, 1733, 1498 1423, 1374, 1247 1207, 1004, 774 705, 660 |
| 34 | 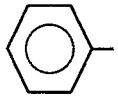 | H | H | H | H | $\underset{|}{\overset{OCH_3}{CH_2CO_2C_2H_4CHCH_3}}$ | $SbF_6$ | 2974, 1733, 1598 1495, 1413, 1373 1243, 1207, 1097 843, 661 |

TABLE 1-continued

Structural formula $$R_5-\underset{\underset{R_2}{|}}{CH}-S^+-\underset{\underset{R_4}{|}}{\overset{\overset{R_3}{|}}{C}}-R_6 \quad X^-$$

| Compound No. | $R_1$ | $R_2$ | $R_3$ | $R_4$ | $R_5$ | $R_6$ | X | Physical Constant IR (KBr cm$^{-1}$) |
|---|---|---|---|---|---|---|---|---|
| 35 | ⌬—CH$_2$— | H | H | H | H | C$_2$H$_5$ / CH$_2$CO$_2$CH$_2$CHC$_4$H$_9$ | SbF$_6$ | 2960, 1730, 1459, 1424, 1245, 1201, 704, 662 |
| 36 | ⌬—CH$_2$— | H | H | H | H | OCH$_3$ / CO$_2$C$_2$H$_4$CHCH$_3$ | SbF$_6$ | 2941, 1740, 1459, 1382, 1318, 1200, 1082, 704, 660 |
| 37 | Cl—⌬—CH$_2$— | H | H | H | H | OCH$_3$ / CO$_2$C$_2$H$_4$CH—CH$_3$ | SbF$_6$ | 2941, 1738, 1598, 1495, 1384, 1318, 1199, 1098, 661 |
| 38 | Cl—⌬—CH$_2$— | H | H | H | H | C$_2$H$_5$ / CO$_2$CH$_2$CHC$_4$H$_9$ | SbF$_6$ | 2935, 1737, 1598, 1495, 1317, 1198, 1098, 662 |
| 39 | ⌬— | H | H | CH$_3$ | H | CO$_2$C$_2$H$_5$ | SbF$_6$ | 2946, 1733, 1450, 1314, 1198, 1079, 754, 687, 659 |

<Test on Curing Capability>

A compound according to the present invention was respectively added to ERL-4221 (alicyclic epoxy compound manufactured by UCC) and UVR-6410 (glycidyl-type epoxy compound manufactured by UCC) at a compounding ratio of 2.5 parts by weight respective to 100 parts by weight of either ERL-4221 or UVR-6410 to prepare a compounded composition. With the compounded compositions, DSC measurement were carried out to determine the top temperatures of exothermic peak, respectively. The followings are the condition for the DSC measurement, and the results obtained were shown in Table 2.

Apparatus for measuring DSC: DSC 220C (Manufactured by Seiko Densi Kogyo)
Atmosphere: In Flow of Nitrogen Gas at a speed of 30 ml/min.
Speed of Temperature Elevation: 10° C./min.
Sample Amount: 0.3–0.8 mg Comparative Sample 1

For the comparative sample to the compound of the present invention, benzyl-4-cyanopyridinium hexafluoroantimonate was used as an initiator of polymerization, then DSC measurement was carried out for a composition compounded with said initiator according to the same procedure as described above in Test on Curing Capability.

Comparative Sample 2

For the comparative sample to the compound of the present invention, N-benzyl-N-methyl anilinium hexafluoroantimonate was used as an initiator of polymerization, then DSC measurement was carried out for a composition compounded with said initiator according to the same procedure as described above in Test on Curing Capability.

Comparative Sample 3

By using benzyl tetramethylene sulfonium hexafluoroantimonate as an initiator of polymerization, a compounded-composition was prepared by mixing it with either ERL-4221 or UVR-6410 according to the same procedure as described in Test on Curing Capability. DSC measurement was carried out for said composition to determine the top temperatures of exothermic peak (See Comparative Examples 1 through 3, and Comparative Examples 4 through 6). All results obtained are shown in Table 2.

TABLE 2

| Compound No. | Epoxy Resin | Top Temp. of DSC Peak (°C.) |
|---|---|---|
| 1 | ERL-4221 | 140 |
| 2 | UVR-6410 | 142 |
| 3 | ERL-4221 | 139 |
| 4 | UVR-6410 | 151 |
| 5 | ERL-4221 | 152 |
| 6 | " | 132 |
| 7 | UVR-6410 | 160 |
| 8 | ERL-4221 | 155 |
| 9 | UVR-6410 | 153 |
| 10 | ERL-4221 | 152 |
| 11 | " | 147 |
| 12 | " | 96 |
| 13 | UVR-6410 | 125 |
| 14 | ERL-4221 | 100 |
| 15 | " | 133 |
| 16 | UVR-6410 | 145 |
| 17 | ERL-4221 | 149 |
| 18 | " | 105 |
| 19 | UVR-6410 | 104 |
| 20 | ERL-4221 | 102 |
| 21 | UVR-6410 | 150 |
| 22 | ERL-4221 | 140 |
| 23 | " | 133 |
| 24 | " | 122 |
| 25 | " | 149 |
| 26 | ERL-4221 | 149 |
| 27 | UVR-6410 | 128 |

TABLE 2-continued

| Compound No. | Epoxy Resin | Top Temp. of DSC Peak (°C.) |
|---|---|---|
| 28 | ERL-4221 | 126 |
| 29 | " | 153 |
| 30 | " | 144 |
| 31 | ERL-4221 | 87 |
| 32 | " | 152 |
| 33 | " | 133 |
| 34 | UVR-6410 | 132 |
| 35 | ERL-4221 | 126 |
| 36 | UVR-6410 | 112 |
| 37 | " | 115 |
| 38 | " | 127 |
| 39 | ERL-4221 | 148 |
| Comparison Sample 1 | ERL-4221 | 174 |
| " | UVR-6410 | 227 |
| Comparison Sample 2 | ERL-4221 | 168 |
| " | UVR-6410 | 201 |
| Comparison Sample 3 | " | 189 |

<Advantageous Physical Property of Cured Products>

Sulfonium salt compound in an amount of 2.0 parts by weight respective to 100 parts of UVR-6410 was added to UVR-6410 to prepare a compounded composition. 10 g of the compounded composition were each distributed into Teflon cups, then were placed for 30 min. in an oven maintained at different temperature, respectively. The dynamic mechanical analysis (DMA) of cured-resin was measured, and temperature of glass transition (Tg) was determined from the peak of loss modulus, respectively.

The conditions for measuring DMA were as follows. The results are shown in Table 3.
Apparatus for measuring DMA: DMA 983 (TA Instrument Japan Inc.)
Frequency: 1 Hz
Speed of Temperature Elevation: 5° C./min.

TABLE 3

| Compound No. | Temp. for Curing | Temp. of Glass Transition |
|---|---|---|
| 6 | 130° C., 30 min. | 141 |
| 13 | 90° C., 30 min. | 145 |
| 22 | 150° C., 30 min. | 129 |
| 23 | " | 130 |
| 27 | 110° C., 30 min. | 144 |
| 32 | 150° C., 30 min. | 135 |
| 34 | 130° C., 30 min. | 143 |
| 36 | 70° C., 30 min. | 144 |
| 38 | 90° C. × 30 min. | 141 |
| 39 | 150° C. × 30 min. | 134 |

Industrial Utilization of the Invention

The novel sulfonium salt compound of the present invention, which has substituents, such as $COOR_8$ and $OR_9$, at the carbon atoms being connected with each other via a carbon atom, which is directly bounding to a sulphur atom or methylene, is found to be effective as an initiator of polymerization for cationic polymerizable compounds. As can be seen from the Examples, Test on Curing Capability and Physical Property of Cured-Products, said sulfonium salt compound can polymerize and cure cationic polymerizable compounds under heating in a very short time and even at low temperature. Furthermore, by changing the substituents of said sulfonium salt compound, optional selection of temperature for curing becomes allowable and the synthesis of the sulfonium salt compounds can be further made easier and less costly.

The initiators of polymerization according to the present invention are each composed of a sulfonium salt compound, however, the sulfonium salt compound contains functional groups, such as hydroxy, carboxyl and ester group, and therefore the initiator gives less or no smell as well as the decomposed-products thereof.

What is claimed is:

1. Sulfonium salt compounds represented by a general formula (I);

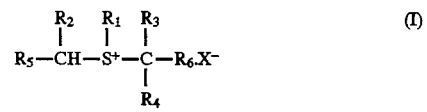

wherein $R_1$ is unsubstituted or substituted benzyl, unsubstituted or substituted naphthylmethyl, unsubstituted or substituted cinnamyl, 9-fluorenyl, or unsubstituted or substituted phenyl, $R_2$ and $R_3$ are each independently hydrogen or alkyl;

$R_4$ is hydrogen, alkyl or phenyl, $R_5$ is hydrogen, alkyl, alkenyl, phenyl or $-(CH_2)_n-R_7$ wherein $R_7$ is $COOR_8$, $OR_9$, nitrile or $OCOR_{10}$, wherein $R_8$, $R_9$ and $R_{10}$ are each independently hydrogen, unsubstituted or substituted alkyl or phenyl, and n denotes 0 or 1, $R_6$ is $-(CH_2)_m-R_{11}$ wherein $R_{11}$ is $COR_{12}$, $COOR_{13}$, $OR_{14}$, nitrile, $OCOR_{15}$ or $SOR_{16}$, wherein $R_{12}$, $R_{13}$, $R_{14}$, $R_{15}$ and $R_{16}$ are each independently unsubstituted or substituted alkyl or phenyl, and m denotes 0 or 1, and X is $Sb_6$, $AsF_6$, $PF_6$ or $BF_4$.

2. Initiators of polymerization comprising at least one of the sulfonium salt compounds represented by the general formula (I) as claimed in claim 1.

* * * * *

UNITED STATES PATENT AND TRADEMARK OFFICE
CERTIFICATE OF CORRECTION

PATENT NO.  : 5,639,903
DATED       : June 17, 1997
INVENTOR(S) : Eiji Takahashi; Hiroo Muramoto It is certified that error appears in the above-indentified patent and that said Letters Patent is hereby corrected as shown below:

Column 2, Line 51, after "wherein" insert  -- $R_{12}$ --.

Signed and Sealed this

Thirty-first Day of March, 1998

Attest:

BRUCE LEHMAN

Attesting Officer

Commissioner of Patents and Trademarks